(12) United States Patent
Macklin et al.

(10) Patent No.: US 10,103,379 B2
(45) Date of Patent: Oct. 16, 2018

(54) STRUCTURED SILICON PARTICLES

(71) Applicant: NEXEON LIMITED, Abingdon, Oxfordshire (GB)

(72) Inventors: William James Macklin, Wantage (GB); Fiona Scott, Redhill (GB); Christopher Michael Friend, Abingdon (GB)

(73) Assignee: Nexeon Limited, Abingdon, Oxfordshire (GB)

( * ) Notice: Subject to any disclaimer, the term of this patent is extended or adjusted under 35 U.S.C. 154(b) by 200 days.

(21) Appl. No.: 14/371,822

(22) PCT Filed: Feb. 28, 2013

(86) PCT No.: PCT/GB2013/050507
§ 371 (c)(1),
(2) Date: Jul. 11, 2014

(87) PCT Pub. No.: WO2013/128201
PCT Pub. Date: Sep. 6, 2013

(65) Prior Publication Data
US 2014/0349183 A1    Nov. 27, 2014

(30) Foreign Application Priority Data
Feb. 28, 2012  (GB) .................................. 1203447.6

(51) Int. Cl.
*H01M 4/36*  (2006.01)
*H01M 4/131*  (2010.01)
(Continued)

(52) U.S. Cl.
CPC .............. *H01M 4/362* (2013.01); *A61K 9/14* (2013.01); *A61K 47/02* (2013.01); *C09C 1/28* (2013.01);
(Continued)

(58) Field of Classification Search
CPC ..................................................... H01M 4/362
See application file for complete search history.

(56) References Cited

U.S. PATENT DOCUMENTS 4,002,541 A    1/1977  Streander
4,192,720 A    3/1980  Bucker et al.
(Continued)

FOREIGN PATENT DOCUMENTS

CN    1569623 A    1/2005
CN    1967910 A    5/2007
(Continued)

OTHER PUBLICATIONS

Merriam Webster particle.*
(Continued)

*Primary Examiner* — Sarah A. Slifka
*Assistant Examiner* — Brian R Ohara
(74) *Attorney, Agent, or Firm* — William R. Haulbrook; Michael D. Schmitt; Choate, Hall & Stewart LLP

(57) ABSTRACT

A composite particle is provided. The particle comprises a first particle component and a second particle component in which: (a) the first particle component comprises a body portion and a surface portion, the surface portion comprising one or more structural features and one or more voids, whereby the surface portion and body portion define together a structured particle; and (b) the second component comprises a removable filler; characterized in that (i) one or both of the body portion and the surface portion comprise an active material; and (ii) the filler is contained within one or more voids comprised within the surface portion of the first component. The use of the particle in applications such as electrochemical cells, metal-ion batteries such as secondary battery applications, lithium air batteries, flow cell batteries, fuel cells, solar cells, filters, sensors, electrical and thermal (Continued)

capacitors, micro-fluidic devices, gas or vapor sensors, thermal or dielectric insulating devices, devices for controlling or modifying the transmission, absorption or reflectance of light or other forms of electromagnetic radiation, chromatography or wound dressings is disclosed.

24 Claims, 2 Drawing Sheets

(51) Int. Cl.
| | |
|---|---|
| H01M 4/134 | (2010.01) |
| H01M 4/136 | (2010.01) |
| H01M 4/38 | (2006.01) |
| H01M 4/48 | (2010.01) |
| H01M 4/58 | (2010.01) |
| H01M 10/0525 | (2010.01) |
| H01M 4/04 | (2006.01) |
| H01M 4/13 | (2010.01) |
| A61K 47/02 | (2006.01) |
| A61K 9/14 | (2006.01) |
| C09C 1/28 | (2006.01) |

(52) U.S. Cl.
CPC ........... *H01M 4/131* (2013.01); *H01M 4/134* (2013.01); *H01M 4/136* (2013.01); *H01M 4/364* (2013.01); *H01M 4/38* (2013.01); *H01M 4/386* (2013.01); *H01M 4/387* (2013.01); *H01M 4/48* (2013.01); *H01M 4/58* (2013.01); *H01M 4/581* (2013.01); *H01M 4/582* (2013.01); *H01M 4/5805* (2013.01); *H01M 4/5815* (2013.01); *H01M 10/0525* (2013.01); *C01P 2002/84* (2013.01); *C01P 2006/40* (2013.01); *H01M 4/0404* (2013.01); *H01M 4/0471* (2013.01); *H01M 4/13* (2013.01)

(56) References Cited

U.S. PATENT DOCUMENTS

| | | | |
|---|---|---|---|
| 4,363,708 A | 12/1982 | Rauchle et al. | |
| 4,686,013 A | 8/1987 | Pensabene et al. | |
| 5,395,711 A | 3/1995 | Tahara et al. | |
| 5,514,495 A * | 5/1996 | Klaus | H01M 4/24 |
| | | | 204/290.11 |
| 5,658,691 A | 8/1997 | Suzuki et al. | |
| 5,914,183 A | 6/1999 | Canham | |
| 6,132,724 A | 10/2000 | Blum | |
| 6,190,951 B1 | 2/2001 | Nakahori et al. | |
| 6,334,939 B1 | 1/2002 | Zhou et al. | |
| 6,514,395 B2 | 2/2003 | Zhou et al. | |
| 7,138,208 B2 | 11/2006 | Tanjo et al. | |
| 7,244,513 B2 | 7/2007 | Li et al. | |
| 7,311,999 B2 | 12/2007 | Kawase et al. | |
| 7,332,339 B2 | 2/2008 | Canham | |
| 7,402,829 B2 | 7/2008 | Green | |
| 7,479,351 B2 | 1/2009 | Matsubara et al. | |
| 7,615,206 B2 | 11/2009 | Sandhage et al. | |
| 7,638,239 B2 | 12/2009 | Sato et al. | |
| 7,713,849 B2 | 5/2010 | Habib et al. | |
| 7,824,801 B2 | 11/2010 | Kogetsu et al. | |
| 7,851,086 B2 | 12/2010 | Matsubara et al. | |
| 7,879,734 B2 | 2/2011 | Fukutani et al. | |
| 8,080,337 B2 | 12/2011 | Higuchi et al. | |
| 8,526,166 B2 | 9/2013 | Choi et al. | |
| 8,585,918 B2 | 11/2013 | Green et al. | |
| 8,597,831 B2 | 12/2013 | Green et al. | |
| 8,772,174 B2 | 7/2014 | Green et al. | |
| 8,940,192 B2 | 1/2015 | Toyokawa | |
| 8,940,437 B2 | 1/2015 | Green et al. | |
| 8,945,431 B2 * | 2/2015 | Schulz | C01B 31/00 |
| | | | 252/502 |
| 9,252,426 B2 | 2/2016 | Green | |
| 9,548,489 B2 | 1/2017 | Abdelsalam et al. | |
| 2001/0044045 A1 | 11/2001 | Sato et al. | |
| 2002/0037433 A1 | 3/2002 | Rasmussen et al. | |
| 2002/0074972 A1 | 6/2002 | Narang et al. | |
| 2002/0121460 A1 | 9/2002 | Moy et al. | |
| 2002/0148727 A1 | 10/2002 | Zhou et al. | |
| 2002/0164479 A1 * | 11/2002 | Matsubara | H01M 4/362 |
| | | | 428/367 |
| 2003/0099883 A1 | 5/2003 | Ochoa et al. | |
| 2003/0150378 A1 | 8/2003 | Winterton et al. | |
| 2004/0052867 A1 | 3/2004 | Canham | |
| 2004/0140222 A1 | 7/2004 | Smedley et al. | |
| 2004/0166319 A1 | 8/2004 | Li et al. | |
| 2004/0214085 A1 | 10/2004 | Sheem et al. | |
| 2005/0186378 A1 | 8/2005 | Bhatt | |
| 2005/0186474 A1 | 8/2005 | Jiang et al. | |
| 2006/0019151 A1 | 1/2006 | Imachi et al. | |
| 2006/0099495 A1 | 5/2006 | Suzuki et al. | |
| 2006/0147802 A1 | 7/2006 | Yasuda et al. | |
| 2006/0166098 A1 | 7/2006 | Tabuchi et al. | |
| 2006/0216603 A1 | 9/2006 | Choi | |
| 2006/0251561 A1 | 11/2006 | Farrell et al. | |
| 2007/0011102 A1 | 1/2007 | Matsuhira et al. | |
| 2007/0020521 A1 | 1/2007 | Obrovac et al. | |
| 2007/0031733 A1 | 2/2007 | Kogetsu et al. | |
| 2007/0054190 A1 | 3/2007 | Fukui et al. | |
| 2007/0077490 A1 | 4/2007 | Kim et al. | |
| 2007/0077491 A1 * | 4/2007 | Burchardt | C01B 3/0031 |
| | | | 429/218.2 |
| 2007/0099081 A1 * | 5/2007 | Matsuda | B22F 1/0059 |
| | | | 429/217 |
| 2007/0111101 A1 | 5/2007 | Ohkubo et al. | |
| 2007/0111102 A1 | 5/2007 | Inoue et al. | |
| 2007/0224508 A1 | 9/2007 | Aramata et al. | |
| 2007/0255198 A1 | 11/2007 | Leong et al. | |
| 2007/0281216 A1 | 12/2007 | Petrat et al. | |
| 2008/0038170 A1 | 2/2008 | Sandhage et al. | |
| 2008/0062616 A1 | 3/2008 | Matsuda et al. | |
| 2008/0096110 A1 | 4/2008 | Bito et al. | |
| 2008/0113269 A1 | 5/2008 | Yamamoto et al. | |
| 2008/0124631 A1 | 5/2008 | Fukui et al. | |
| 2008/0145757 A1 | 6/2008 | Mah et al. | |
| 2008/0166474 A1 * | 7/2008 | Deguchi | H01M 4/134 |
| | | | 427/122 |
| 2008/0261112 A1 | 10/2008 | Nagata et al. | |
| 2008/0280207 A1 | 11/2008 | Patoux et al. | |
| 2009/0004566 A1 | 1/2009 | Shirane et al. | |
| 2009/0004568 A1 * | 1/2009 | Hirose | H01M 2/0285 |
| | | | 429/221 |
| 2009/0010833 A1 | 1/2009 | Rosenband et al. | |
| 2009/0137688 A1 * | 5/2009 | Yang | A61K 9/1611 |
| | | | 514/770 |
| 2009/0143227 A1 | 6/2009 | Dubrow et al. | |
| 2009/0169985 A1 | 7/2009 | Yamaguchi et al. | |
| 2009/0186267 A1 | 7/2009 | Tiegs | |
| 2009/0253033 A1 | 10/2009 | Hirose et al. | |
| 2009/0301866 A1 | 12/2009 | Zaghib et al. | |
| 2010/0008841 A1 | 1/2010 | Rosenkilde | |
| 2010/0112442 A1 | 5/2010 | Fujikawa et al. | |
| 2010/0112451 A1 | 5/2010 | Shibutani et al. | |
| 2010/0112475 A1 | 5/2010 | Natsume et al. | |
| 2010/0143773 A1 | 6/2010 | Honbou | |
| 2010/0143798 A1 | 6/2010 | Zhamu et al. | |
| 2010/0178565 A1 | 7/2010 | Green | |
| 2010/0190061 A1 | 7/2010 | Green | |
| 2010/0196760 A1 | 8/2010 | Green | |
| 2010/0243951 A1 | 9/2010 | Watanabe et al. | |
| 2010/0266902 A1 | 10/2010 | Takano et al. | |
| 2010/0278931 A1 | 11/2010 | Ashton et al. | |
| 2010/0285358 A1 | 11/2010 | Cui et al. | |
| 2010/0291441 A1 | 11/2010 | Ugaji et al. | |
| 2010/0297502 A1 | 11/2010 | Zhu et al. | |
| 2010/0330418 A1 * | 12/2010 | Liang | H01M 2/1653 |
| | | | 429/207 |
| 2010/0330425 A1 | 12/2010 | Lopatin et al. | |

(56) References Cited

U.S. PATENT DOCUMENTS

| | | | |
|---|---|---|---|
| 2011/0008531 A1 | 1/2011 | Mikhaylik et al. | |
| 2011/0027537 A1* | 2/2011 | Inoue | C23C 8/04 |
| | | | 428/172 |
| 2011/0039690 A1 | 2/2011 | Niu | |
| 2011/0056563 A1 | 3/2011 | Bari | |
| 2011/0067228 A1 | 3/2011 | Green | |
| 2011/0076560 A1 | 3/2011 | Scordilis-Kelley et al. | |
| 2011/0085960 A1 | 4/2011 | Mukasyan et al. | |
| 2011/0104480 A1 | 5/2011 | Malekos et al. | |
| 2011/0111135 A1 | 5/2011 | Kamiyama et al. | |
| 2011/0111279 A1 | 5/2011 | Smithyman et al. | |
| 2011/0123866 A1 | 5/2011 | Pan et al. | |
| 2011/0163274 A1 | 7/2011 | Plee et al. | |
| 2011/0236493 A1 | 9/2011 | Canham et al. | |
| 2011/0244328 A1 | 10/2011 | Iriyama et al. | |
| 2011/0250498 A1 | 10/2011 | Green et al. | |
| 2011/0269019 A1 | 11/2011 | Green et al. | |
| 2011/0281180 A1* | 11/2011 | Kim | H01M 4/133 |
| | | | 429/338 |
| 2011/0287318 A1 | 11/2011 | Loveness et al. | |
| 2011/0299223 A1 | 12/2011 | Oh et al. | |
| 2012/0040242 A1 | 2/2012 | Kurasawa et al. | |
| 2012/0094178 A1 | 4/2012 | Loveridge et al. | |
| 2012/0100438 A1 | 4/2012 | Fasching et al. | |
| 2012/0107688 A1* | 5/2012 | Loveridge | H01M 4/134 |
| | | | 429/217 |
| 2012/0121999 A1* | 5/2012 | Laurencin | H01M 4/861 |
| | | | 429/423 |
| 2012/0171566 A1 | 7/2012 | Yoshitake et al. | |
| 2012/0255858 A1 | 10/2012 | Maeshima et al. | |
| 2012/0315543 A1 | 12/2012 | Wata et al. | |
| 2013/0196158 A1 | 8/2013 | Yoshida et al. | |
| 2013/0216907 A1 | 8/2013 | Rayner et al. | |
| 2013/0224583 A1 | 8/2013 | Green | |
| 2014/0030599 A1 | 1/2014 | Lee et al. | |
| 2014/0147751 A1 | 5/2014 | Yang et al. | |
| 2014/0162131 A1 | 6/2014 | Friend et al. | |
| 2014/0170303 A1 | 6/2014 | Rayner et al. | |
| 2014/0193711 A1 | 7/2014 | Biswal et al. | |
| 2014/0235884 A1 | 8/2014 | Veinot et al. | |
| 2015/0044571 A1 | 2/2015 | Abdelsalam et al. | |
| 2015/0104705 A1 | 4/2015 | Canham et al. | |
| 2015/0280221 A1 | 10/2015 | Abdelsalam et al. | |
| 2016/0172670 A1 | 6/2016 | Friend | |
| 2016/0197342 A1 | 7/2016 | Lee et al. | |
| 2016/0308205 A1 | 10/2016 | Canham et al. | |
| 2017/0133674 A1 | 5/2017 | Murphy et al. | |
| 2017/0200939 A1 | 7/2017 | Murphy et al. | |
| 2017/0346079 A1 | 11/2017 | Friend et al. | |

FOREIGN PATENT DOCUMENTS

| | | | | |
|---|---|---|---|---|
| CN | 101188281 A | 5/2008 | | |
| CN | 101335342 A | 12/2008 | | |
| CN | 101442124 A | 5/2009 | | |
| CN | 101471457 A | 7/2009 | | |
| CN | 101591478 A | 12/2009 | | |
| CN | 102157731 A | 8/2011 | | |
| CN | 103 165 870 A | 6/2013 | | |
| CN | 103 633 295 A | 3/2014 | | |
| CN | 103840140 A | 6/2014 | | |
| EP | 0281115 A2 | 9/1988 | | |
| EP | 1335438 A1 | 8/2003 | | |
| EP | 1427039 A2 | 6/2004 | | |
| EP | 1750314 A1 | 2/2007 | | |
| EP | 1791199 A1 | 5/2007 | | |
| EP | 2037516 A1 | 3/2009 | | |
| EP | 2051317 A1 | 4/2009 | | |
| EP | 2383224 A1 | 11/2011 | | |
| EP | 2509142 A1 | 10/2012 | | |
| EP | 2873646 A1 | 5/2015 | | |
| EP | 2533331 B1 | 8/2015 | | |
| GB | 980513 A | 1/1965 | | |
| GB | 2000191 A | 1/1979 | | |
| GB | 2395059 A | 5/2004 | | |
| GB | 2464158 A | 4/2010 | | |
| GB | 2470056 A | 11/2010 | | |
| GB | 2483372 A | 3/2012 | | |
| GB | 2495951 A | 5/2013 | | |
| JP | 06-325765 A | 11/1994 | | |
| JP | 11-250896 | 9/1999 | | |
| JP | 2001-266866 A | 9/2001 | | |
| JP | 2002-151055 A | 5/2002 | | |
| JP | 2003-077463 A | 3/2003 | | |
| JP | 2003-303586 A | 10/2003 | | |
| JP | 2004-185984 A | 7/2004 | | |
| JP | 2004/214054 A | 7/2004 | | |
| JP | 2004281317 A | 10/2004 | | |
| JP | 2005-63955 A | 3/2005 | | |
| JP | 03714665 B2 | 11/2005 | | |
| JP | 2006-100244 A | 4/2006 | | |
| JP | 2006172860 A | 6/2006 | | |
| JP | 2006-269216 A | 10/2006 | | |
| JP | 2007-042285 A | 2/2007 | | |
| JP | 2007-294423 A | 11/2007 | | |
| JP | 2007-335283 A | 12/2007 | | |
| JP | 2007318057 A | 12/2007 | | |
| JP | 2007335198 A | 12/2007 | | |
| JP | 2008-166013 A | 7/2008 | | |
| JP | 2008186732 A | * 8/2008 | | H01M 4/02 |
| JP | 2008-293872 A | 12/2008 | | |
| JP | 2008305746 A | 12/2008 | | |
| JP | 2010205609 A | 9/2010 | | |
| JP | 2011-009228 A | 1/2011 | | |
| JP | 2011-192629 A | 9/2011 | | |
| JP | 2011/198614 A | 10/2011 | | |
| JP | 2012084521 A | 4/2012 | | |
| JP | 2012084522 A | 4/2012 | | |
| KR | 2008-0091883 A | 10/2008 | | |
| KR | 2013 0107892 A | 10/2013 | | |
| KR | 20140070227 A | 6/2014 | | |
| SU | 471402 A1 | 3/1973 | | |
| SU | 544019 A | 7/1975 | | |
| WO | WO-97/01193 A1 | 1/1997 | | |
| WO | WO-2005/075048 A1 | 8/2005 | | |
| WO | WO-2005/096414 A2 | 10/2005 | | |
| WO | WO-2006/068066 A1 | 6/2006 | | |
| WO | WO-2006/097380 A1 | 9/2006 | | |
| WO | WO-2006/135375 A2 | 12/2006 | | |
| WO | WO-2007/037787 A1 | 4/2007 | | |
| WO | WO-2007/083152 A1 | 7/2007 | | |
| WO | WO-2007/083155 A1 | 7/2007 | | |
| WO | WO-2007/094641 A1 | 8/2007 | | |
| WO | WO-2008/044683 A1 | 4/2008 | | |
| WO | WO-2009/010758 A2 | 1/2009 | | |
| WO | WO-2009/010759 A1 | 1/2009 | | |
| WO | WO-2009/033082 A2 | 3/2009 | | |
| WO | WO-2009/050585 A1 | 4/2009 | | |
| WO | WO-2009/063801 A1 | 5/2009 | | |
| WO | WO-2009/128800 A1 | 10/2009 | | |
| WO | WO-2010/026332 A1 | 3/2010 | | |
| WO | WO-2010/040985 A1 | 4/2010 | | |
| WO | WO-2010/128310 A1 | 11/2010 | | |
| WO | WO-2010/130975 A1 | 11/2010 | | |
| WO | WO-2010/130976 A1 | 11/2010 | | |
| WO | WO-2010/139987 A2 | 12/2010 | | |
| WO | WO-2011/042742 A1 | 4/2011 | | |
| WO | WO-2011/117436 A1 | 9/2011 | | |
| WO | WO-2012/028857 A1 | 3/2012 | | |
| WO | WO-2012/028858 A1 | 3/2012 | | |
| WO | WO-2012/084570 A1 | 6/2012 | | |
| WO | WO-2012/093224 A1 | 7/2012 | | |
| WO | WO-2012/175998 A1 | 12/2012 | | |
| WO | WO-2013/021630 A1 | 2/2013 | | |
| WO | WO-2013/024305 A2 | 2/2013 | | |
| WO | WO-2013/114094 A1 | 8/2013 | | |
| WO | WO-2013/128201 A2 | 9/2013 | | |
| WO | WO-2013/140177 A2 | 9/2013 | | |
| WO | WO-2013/146658 A1 | 10/2013 | | |
| WO | WO-2013/179068 A2 | 12/2013 | | |
| WO | WO-2013/179068 A3 | 1/2014 | | |

(56) References Cited

FOREIGN PATENT DOCUMENTS

| WO | WO-2014/068318 A1 | 5/2014 |
|----|-------------------|--------|
| WO | WO-2015/041450 A1 | 3/2015 |
| WO | WO-2015/082920 A1 | 6/2015 |

OTHER PUBLICATIONS

JP2008186732 translation (Year: 2008).*
Gao et al., Alloy formation in Nanostructured Silicon, Journal of Advanced Materials, 13(11):816-819 (2001).
International Search Report, PCT/GB2014/053594, 6 pages, dated May 22, 2015.
Notice of Opposition, EP 2533331 B1, 6 pages, dated May 27, 2016.
Ohara, S. et al., A thin film silicon anode for Li-ion batteries having a very large specific capacity and long cycle life, Journal of Power Sources, (136):303-306 (2004).
Bang, B.M. et al., Scalable Approach to Multi-Dimensional Bulk Si Anodes via Metal-Assisted Chemical Etching, Energy & Environmental Science, 4:5013-5019 (2011).
Chartier, C. et al., Metal-assisted chemical etching of silicon in HF-H2O2, Electrochimica Acta, 53(17):5509-5516 (2008).
Chen et al., Mesoporous Silicon Anodes Prepared by Magnesiothermic Reduction for Lithium Ion Batteries, Journal of the Electrochemical Society, 158(9):A1055-A1059 (2011).
Chen, X. et al., A Patterned 3D Silicon Anode Fabricated by Electrodeposition on a Virus-Structured Current Collector, Advanced Function Materials, 21:380-387 (2011).
Choi et al., Silica nanofibres from electrospinning/sol-gel process. J. Mater. Sci. Letters, 22:891-893 (2003).
Graetz, J. et al., Highly reversible lithium storage in nanostructured silicon, Journal of the Electrochemical Society, 6(9):194-197 (2003).
Hatchard, T. D. and Dahn, J. R., In Situ XRD and Electrochemical Study of the Reaction of Lithium with Amorphous Silicon, Journal of the Electrochemical Society, 151(6):A838-A842 (2004).
Huang, Z. et al., Metal-Assisted Chemical Etching of Silicon: A Review, Adv. Mater. 23:285-308 (2011).
Jia et al., Novel Three-Dimensional Mesoporous Silicon for High Power Litium-Ion Battery Anode Material, Advs. Energy Mater., 1:1036-1039 (2011).
Krissanasaeranee et al.. Preparation of Ultra-Fine Silica Fibers Using Electrospun Ply(Vinyl Alcohol)/Silatrane Composite Fibers as Precursor, J. Am. Ceram. Soc., 91(9):2830-2835 (2008).
Lestriez, B. et al., Hierarchical and Resilient Conduction Network of Bridged Carbon Nanotubes and Nanofibers for High-Energy Si Negative Electrodes, Electrochemical and Solid-State Letters, 12(4):76-80 (2009).
Ma et al., Silver nanoparticles decorated, flexible $SiO_2$ nanofibers with long-term antibacterial effect as reusable wound cover, Colloids and Surfaces A: Physicochem. Eng. Aspects 387:57-64 (2011).
Mallet, J. et al., Growth of silicon nanowires of controlled diameters by electrodeposition in ionic liquid at room temperature, Nanoletters, 8(10):3468-3474 (2008).
Oudenhoven, Jos F. M. et al., All-solid-State Lithium-Ion Microbatteries: A Review of Various Three-Dimensional Concepts, Adv. Energy Mater. 1:10-33 (2011).
Purkid et al., Synthesis and Characterization of $SiO_2$ Nanowires Prepared from Rice Husk Ash. J. Metals, Materials and Minerals, 19(2):33-37 (2009).
Richman et al., Ordered Mesoporous Silicon through Magensium Reduction of Polymer Templated Silica Thin Films, Nano Lett., 8(9):3075-3079 (2008).
Robinson, D. and Walsh, F.C., The Performance of a 500 Amp Rotating Cylinder Electrode Reactor. Part 1: Current-Potential Data and Single Pass Studies, Hydrometallurgy, 26:93 (1991).
Rongguan, L. et al., Electrodeposited porous-microspheres Li—Si films as negative electrodes in lithium-ion batteries, Journal of Power Sources, 196(8):3868-3873 (2011).
Schmuck, M. et al, Alloying of electrodeposited silicon with lithium—a principal study of applicability as a node material for lithium ion batteries, J. Solid State Electrochem, 14:2203-2207 (2010).

Shin, H. C. et al., Nanoporous Structures Prepared by an Electrochemical Deposition Process, Advanced Materials, 15:19, 1610-1614 (2003).
Teschke, O. et al., Test cell simulating the operating conditions of water electrolysers for the evaluation of gas evolving electrocatalysts, Journal of Applied Electrochemistry, 13(3):371-376 (1983).
Wachtler, M. et al., Anodic materials for rechargeable Li-batteries, Journal of Power Sources 105:151-160 (2002).
Winter, M. et al., Insertion Electrode Materials for Rechargeable Lithium Batteries, Adv. Mater. 10(10):725-763 (1988).
Xiao, et al., Stabilization of Silicon Anode for Li-ion Batteries, Journal of the Electrochemical Society, 157(10):1047-1051 (2010).
Yang, J. et al., Si/c composites for high capacity lithium storage materials, Journal of the Electrochemical Society, 6(8):154-156 (2003).
Yu et al., Reversible Storage of Lithium in Silver-Coated Three-Dimensional Macroporous Silicon, Adv. Mater., 22:2247-2250 (2010).
Zhang et al., Vapor-induced solid-liquid-solid process for silicon-based nanowire growth, Journal of Power Sources 195:1691-1697 (2010).
United Kingdom Search Report for GB1203447.6, dated Jun. 25, 2012, 2 pages.
Cui, et al. Doping and Electrical Transport in Silicon Nanowires, Journal of Physical Chemistry, 104(22):5213-5216 (2000).
Cullis et al., Structural and Luminescence properties of porous silicon, Applied Physics Reviews. 82(3):909-965 (1997).
Gao, B, Synthesis and Electrochemical Properties of Carbon Nanotubes and Silicon Nanowires, Ph.D. Thesis in Applied and Material Sciences, University of North Carolina Chapel Hill (2001).
Jung, K. H. et al., Developments in Luminescent Porous Si, J. Electrochem. Soc., 140(10):3046-3064 (1993).
Kuriyama, K. et al.. Anomalous electrical resistivity and photovoltaic phenomenon in the fast mixed conductor lithium silicide Li12Si17, Physical Review, 38(18):1436-38 (1988).
Meijer, J.A. et al., Electrical resistivity and 7Li Knight shift of liquid Li—Si alloys, J. Phys. Condens. Matter I, 5283-5289 (1989).
Shih, S. et al., Transmission electron microscopy study of chemically etched porous Si, Applied Physical Letters, 62(5):467-69 (1993).
Sinha, S. et al., Synthesis of Silicon Nanowires and Novel Nano-Dendrite Structures, CP544 Electronic Properties of Novel Materials Molecular Nanostructures, 431-436 (2000).
Sinha, S. et al., Synthesis of silicon nanowires and novel nano-dendrite structures, Journal of Nanoparticle Research 6: 421-425 (2004).
Tarascon, J M. et al., an update of the Li metal-free rechargeable battery based on $Li_{1+x}Mn_2O_4$ cathodes and carbon anodes, Journal of Power Sources, 43-44:689-700 (1993).
Van Schalkwijk. Walter A. and Scrosati, Bruno, Advances in Lithium-Ion Batteries (edited 2002 Excerpts).
Wakihara, M., Recent development in lithium ion batteries. Materials Science and Engineering, R33:109-134 (2001).
GB Patent Application No. 0601319.7, filed Jan. 23, 2006, 14 pages.
Li, H. et al., The crystal structural evolution of nano-Si anode caused by lithium insertion and extraction at room temperature, Solid State Ionics 135:181-191 (2000).
Morales, Alfredo M. and Lieber, Charles M., A Laser Ablation Method for the Synthesis of Crystalline Semiconductor Nanowires, Science, 279(9):208-211 (1998).
Winter, Martin and Brodd, Ralph J., Batteries versus Fuel Cells versus Electrochemical Capacitors, Chem. Rev. 104:4245-4269 (2004).
Zhang, Sheng Shui, A review on electrolyte additives for lithium-ion batteries, Journal of Power Sources, 162:1379-1394 (2006).
Zhou, G. W. et al., Controlled Li doping of Si nanowires by electrochemical insertion methods, Applied Physics Letters, 75(16):2447-2449 (1999).
Webb, P.A. and Orr, C., Modern Methods of Particle Characterization, Micromeritics, 17 pages (1998).
Ren, W. et al., Preparation of porous silicon/carbon microspheres as high performance anode materials for lithium ion batteries, Journal

(56) References Cited

OTHER PUBLICATIONS of Materials Chemistry A: Materials for Energy and Sustainability, 3(11):5859-5865 (2015).

* cited by examiner

STRUCTURED SILICON PARTICLES

CROSS-REFERENCE TO RELATED APPLICATION

This patent application is a National Stage Entry of International Patent Application No. PCT/GB2013/050507, filed on Feb. 28, 2013, which claims priority to GB patent application No. 1203447.6, filed on Feb. 28, 2012, the entire contents of each of which are hereby incorporated by reference herein.

FIELD OF THE INVENTION

The present invention relates to structured active particles, particularly but not exclusively to structured silicon particles for use in a range of applications such as electrochemical cells, metal-ion batteries such as secondary battery applications, lithium air batteries, flow cell batteries, fuel cells, solar cells, filters, sensors, electrical and thermal capacitors, micro-fluidic devices, gas or vapour sensors, thermal or dielectric insulating devices, devices for controlling or modifying the transmission, absorption or reflectance of light or other forms of electromagnetic radiation, chromatography or wound dressings. More particularly the invention relates to composite particles comprising a structured active particle and a filler, especially structured active silicon particles, which include a removable filler, methods of preparing same and their use in the preparation of electrodes. More especially the invention relates to structured active particles, particularly structured active silicon particles and their use in battery applications, particularly lithium ion battery applications.

BACKGROUND

It should be appreciated that the term "structured particle" as used herein includes within its definition porous particles substantially as described in WO 2010/128310; porous particle fragments substantially as described in United Kingdom patent application number GB 1115262.6; particles including both branched and un-branched pillars extending from a particle core (hereafter referred to as pillared particles) substantially as described in US 2011/0067228, US 2011/0269019, US 2011/0250498 or prepared using the techniques described in U.S. Pat. No. 7,402,829, JP 2004281317, US 2010/0285358, US 2010/0297502, US 2008/0261112 or WO 2011/117436; fibres substantially as described in U.S. Pat. No. 8,101,298, the fibres including pores or voids distributed over the surface thereof; flakes and ribbons substantially as described in US 2010/0190061 (also having pores or voids distributed over the surface thereof) and fractals substantially as described in GB 1115262.6.

All particles disclosed herein are suitably defined in terms of their size and shape. Not all particles will be truly spherical and will generally be characterised by a principal or larger dimension (or diameter) and a minor (or smallest) dimension or diameter. For a spherical or substantially spherical particle the principal and minor dimensions will generally be the same or similar. For an elongate particle such as a fibre, however, the principal dimension will generally be defined in terms of the fibre length and the minor dimension will generally be defined in terms of the fibre thickness. The particles may also be defined in terms of their aspect ratio, which is the ratio of the magnitude of the principal dimension to that of the minor dimension; for a substantially spherical particle the aspect ratio will be of the order of 1. An elongate particle will generally have an aspect ratio of greater than 1, for example greater than 2, greater than 3, greater than 5 or greater than 10.

The dimensions of particles may be measured by scanning electron microscopy or transmission electron microscopy. Mean average lengths and thicknesses may be obtained by measuring lengths and thicknesses in a sample of a particulate material.

A composition or powder comprises a plurality of particles having a size distribution.

A distribution of the particle sizes within a powder may be measured by laser diffraction, in which the particles being measured are typically assumed to be spherical, and in which particle size is expressed as a spherical equivalent volume diameter, for example using the Mastersizer™ particle size analyzer available from Malvern Instruments Ltd. A spherical equivalent volume diameter is the diameter of a sphere with the same volume as that of the particle being measured. If all particles in the powder being measured have the same density then the spherical equivalent volume diameter is equal to the spherical equivalent mass diameter which is the diameter of a sphere that has the same mass as the mass of the particle being measured. For measurement the powder is typically dispersed in a medium with a refractive index that is different to the refractive index of the powder material. A suitable dispersant for powders of the present invention is water. For a powder with different size dimensions such a particle size analyser provides a spherical equivalent volume diameter distribution curve.

Size distribution of particles in a powder measured in this way may be expressed as a diameter value Dn in which at least n % of the volume of the powder is formed from particles have a measured spherical equivalent volume diameter equal to or less than D. All dimensions quoted herein are referred to as a $D_{50}$ value, that is the diameter in which at least 50% of the volume of the powder is formed from particles having a measured spherical equivalent diameter equal or less than the value of $D_{50}$.

Further the term "active particle" as used herein should be understood to mean a particle comprising a material, which possesses an inherent property (for example an electrical, electronic, electrochemical or optical property) so that the operation of a product including a particle comprising that material is dependent on its inherent property. For example, if the particle comprises a material that is inherently electroactive, that electroactivity can form the basis of a secondary battery including that particle. By the term "electroactive" it should be understood to mean a material which, when used in battery applications is able to insert into its structure, and release therefrom, metal ions such as lithium, sodium, potassium, calcium or magnesium during the respective battery charging phase and discharging phases. Preferably the material is able to insert and release lithium. If the particle comprises a material that exhibits photovoltaic activity, particles including such a photovoltaic material can be used in the formation of solar cells, for example. Further if the material is placed in an environment in which it naturally corrodes, the resulting corrosion current can be harnessed and the material can be used as a battery to power an external device; devices of this type are commonly known as "fuel cells" in which the corroding material provides the fuel. The operation of devices such as sensors, particularly silicon sensors depends on the induced changes in the resistivity or conductivity that arise as a result of the presence of sensed contaminants, for example, the inherent property of such devices being the resistivity or conductivity of the sensor material.

The term "structured active particle" as used herein will therefore be understood to mean a structured particle as defined herein above, which comprises a material having an inherent property that forms the operational basis of a device of which it forms a part.

The term "composite material" as used herein should be understood to mean a material comprising a structured active particle and one or more additional components selected from the group comprising a binder, a conductive material, a filler, an auxiliary electroactive material or a mixture thereof. Composite materials are generally formed by drying a slurry including the components described above to remove the slurry solvent.

The term "electrode material" as used herein should be understood to mean a composite material in which the structured active particle comprises an electroactive material.

The term "composite mix" as used herein should be understood to mean a composition comprising a slurry of a composite material in a liquid carrier.

The term "electrode mix" as used herein should be understood to mean a composite mix in which the structured active particle comprises an electroactive material.

The term "stable suspension" as used herein should be understood to mean a dispersion of particles in a liquid carrier, wherein the particles do not or do not tend to form aggregates.

Structured active particles, such as those described above may be used in applications including electrochemical cells, metal ion batteries such as lithium-ion batteries, lithium air batteries, flow cell batteries, other energy storage devices such as fuel cells, thermal batteries, photovoltaic devices such as solar cells, filters, sensors, electrical and thermal capacitors, microfluidic devices, gas/vapour sensors, thermal or dielectric insulating devices, devices for controlling or modifying the transmission, absorption or reflectance of light or other forms of electromagnetic radiation, chromatography or wound dressings. U.S. Pat. No. 5,914,183 discloses a luminescent device comprising a wafer including quantum wires formed at the surface thereof.

Porous silicon particles may also be used for the storage, controlled delivery or timed release of ingredients or active agents in consumer care, nutritional or medical products. Examples of porous silicon particles of this type are disclosed in US 2010/0278931, US 2011/0236493, U.S. Pat. No. 7,332,339, US 2004/0052867, US 2007/0255198 and WO 2010/139987. These particles tend to be degraded or absorbed in the physiological environment of the body. Degradable or absorbable particles are inherently unsuitable for use in the applications such as electrochemical cells, metal ion batteries such as lithium-ion batteries, lithium air batteries, flow cell batteries, other energy storage devices such as fuel cells, thermal batteries, photovoltaic devices such as solar cells, filters, sensors, electrical and thermal capacitors, microfluidic devices, gas/vapour sensors, thermal or dielectric insulating devices, devices for controlling or modifying the transmission, absorption or reflectance of light or other forms of electromagnetic radiation, chromatography or wound dressings.

Secondary batteries including composite electrodes comprising a layer of structured silicon particles on a current collector are known and are described in, for example: US20100112475, U.S. Pat. No. 4,002,541, U.S. Pat. No. 4,363,708, U.S. Pat. No. 7,851,086, US 2004/0214085, US 2009/0186267, US 2011/0067228, WO 2010/130975, WO 2010/1309766 and WO 2010/128310.

It is believed that an ongoing need for secondary batteries having ever greater capacities and cycle life may be achieved by manufacturing composite electrodes using a high solids content slurry. Electrode materials used in the formation of these batteries are characterised by high homogeneity and intimate connectivity.

It is known that batteries including anodes comprising structured silicon particles exhibit better capacity and life cycle characteristics compared to batteries comprising native or unstructured silicon particles as structured silicon particles have a reduced tendency to crack and are more able to accommodate stress build-up during the charging and discharging phases of the battery. Further, the structured silicon particles tend to be highly porous (or can be engineered so that they are) and are characterised by a large surface area; although this provides a large surface area over which insertion and release of metal ions can occur and can improve the rate of charge/discharge, the structures may be inherently fragile. In this case, the storage and bulk transport of such structures or the preparation of electrode materials comprising structured silicon particles can be problematic: although voids or channels in the structured electroactive material have been found to be advantageous in minimising the build up of stress within the electrode material, they represent a physical barrier to the passage of charge within the electrode material, which means that the insertion and release characteristics of the structured material are not always fully optimised and the internal conductivity of the electrode material is reduced. In addition, if the pores are small, efficient wetting of the electroactive material by a liquid electrolyte may not occur, which also reduces the efficiency of charge transfer therein; penetration by a gel electrolyte is almost impossible. Further, it sometimes happens that during processing of structured silicon particles, such as silicon pillared particles, highly porous particles, fibres or porous fibres complete or partial disintegration of the particle occurs as a result of pillar loss. This pillar loss may be due to either the frictional forces experienced by each particle due to collisions with the other particles in the slurry or may simply be the result of the inherently fragile nature of a highly porous particle. Inherent fragility means that the processing, storage and transportation of such materials is difficult.

There may further be a need to improve dispersion of active particles within a composite material by reducing or eliminating clumping or agglomeration of the active particles during incorporation within the composite, for example whilst mixing into a slurry. Agglomeration may occur due to the particular dimensions and shapes of the active particles and/or the state of their surfaces (for example the surface reactivity, surface roughness and/or presence of pores).

There is a need, therefore, for a structured active particle which is able to optimise both insertion and release of lithium and other charge carriers, particularly where the structured particle is used in battery applications. There is a further need for a structured active particle, which is able to optimise electrical conductivity within a material of which it forms a part in both battery and other related applications. In addition, there is a need for a structured active particle that can promote active wetting of a material of which it forms a part in a battery and other applications. Further, there is a need for a structured active particle, which is able to resist degradation and to avoid being agglomerated during manufacture of a composite electrode. There is a further need for a method of preparing structured active material. The present invention addresses these needs.

A first aspect of the invention provides a composite particle comprising a first particle component and a second particle component in which:

(a) the first particle component comprises a body portion and a surface portion, the surface portion comprising one or more structural features and one or more voids, whereby the surface portion and body portion define together a structured particle; and (b) the second component comprises a removable filler; characterised in that (i) one or both of the body portion and the surface portion comprise an active material; (ii) the filler is contained within one or more voids comprised within the surface portion of the first component and (iii) the filler either has a sublimation or disintegration temperature of at least 50° C. and/or is soluble in an ionic liquid or an electrolyte solution.

The composite particles of the first aspect of the invention do not degrade to a significant extent and are suitable for use in applications such as electrochemical cells, metal ion batteries such as lithium-ion batteries, lithium air batteries, flow cell batteries, other energy storage devices such as fuel cells, thermal batteries, photovoltaic devices such as solar cells, filters, sensors, electrical and thermal capacitors, microfluidic devices, gas/vapour sensors, thermal or dielectric insulating devices, devices for controlling or modifying the transmission, absorption or reflectance of light or other forms of electromagnetic radiation or chromatography or wound dressings applications. The composite particles may additionally make it easier to disperse the active materials evenly throughout a composite material by the reduction or elimination of agglomeration. Dispersion may be aided for example Furthermore, by making the second component removable, it will not impede the function of the active material within the application after manufacture. The composite particles are particularly suitable for use in secondary battery applications. The composite particles are unsuitable for delivering substances to the human body as they do not tend to disintegrate in physiological fluids.

First Particle Component

The surface portion of the first particle component may be defined as that part of the particle that contains structural features or the greatest number of structural features within the particle volume. The presence of voids within the surface portion imparts an inherent porosity to the first particle component.

The structural features and one or more voids of the surface portion suitably extend between the body portion and the particle boundary (outer surface of the surface portion). The distance over which these features extend defines the thickness of the surface portion. The structural features may comprise pillars, which may be branched or un-branched. Preferably the structural features comprise un-branched pillars, more preferably substantially straight, unbranched pillars. Each structural feature may be separated from an adjacent feature by one or more voids. Particles having substantially straight pillars extending from the body portion are disclosed to in US 2011/0067228 and are typically referred to as pillared particles. Alternatively, a structural feature may be fused to an adjacent structural feature; either along the entirety of its length where the structural feature is a substantially straight, un-branched pillar or at points over the surface, where the structural feature is branched. Particles comprising branched pillars having points of fusion over the pillar surface define, in effect, a particle having a plurality of pores or voids distributed over the surface thereof; such particles are referred to in WO 2010/128310 as porous particles. The structural features and one or more voids are suitably distributed over at least 20% of the area occupied by the surface portion, preferably at least 30% and especially at least 50%.

The one or more voids in the surface portion may suitably be in the form of pores or channels. Pores are suitably distributed over the surface portion of the first particle component and are in direct or indirect (via other pores, for example) communication with the particle boundary. Channels suitably extend from the body portion to the particle boundary. Channels may be straight or convoluted, but are preferably substantially straight. Both the pores and channels provide a path whereby a filler can penetrate and occupy void spaces comprised within the surface portion of the first particle component. Composite particles comprising as first particle component a pillared particle having a solid core and substantially straight pillars and channels extending through the surface portion are preferred.

Structure Mass Fraction and Structure Volume Fraction of the First Particle Component The structural features on the surface of the first particle component can be defined in terms of the Structure Mass Fraction (SMF) of a structured particle is provided by the following equation:

$$SMF=[(\text{Mass of structures attached to and extending from the particle core})/(\text{Total mass of structured particle})]\times 100\%$$

Accordingly, in the case of an active silicon structured particle material it will be understood that the SMF is the mass of silicon structures divided by the mass of the whole particle.

The SMF may be determined by various methods. If the structures are grown on, deposited on or attached to the particle cores then the SMF may be calculated by measuring the mass of a plurality of particle cores before growth or attachment and the mass of the structured particles after growth or attachment and subtracting one from the other to calculate the mass of structures in the above equation.

If the structured particle is made by etching a silicon particle to form silicon structures on the surface of a particle core then the SMF may be determined by an oxidation technique. This involves firstly measuring the mass of a quantity of structured particles and then measuring a change in mass over time of the quantity of structured particles during oxidation, for example by heating structured particles in an oxygen-containing atmosphere, e.g. by heating to 1040° C. in air. The structures are fully oxidised first, and oxidise at a relatively rapid rate (shown as a relatively rapid increase in the rate of mass increase). Oxidation of the structures is deemed to be complete when the rate of mass increase is observed to reduce and become linear with time. From this time onwards the rate of mass increase is due only by steady oxidation of the silicon into the particle core. The observed increase in mass up to this point is mostly due to oxidation of the structures and using the difference in density between silicon and silicon oxide, the mass of the structures before oxidation and hence the PMF can be determined. For a powder sample with a broad size distribution, the particles cores of the smaller structured particles may additionally be oxidised and a correction factor may need to be applied to take account of the core oxidation. The correction factor can be estimated by doing the measurement on a sample comprising the particle cores with the structures absent or removed. This method is particularly suitable for structured particles having silicon pillars.

The SMF may also be determined by measuring the mass of a quantity of structured particles, removing the structures from the particle cores, for example by mechanical agitation (such as ultrasonication), scraping or chemical etching, separating the detached structures from the particle cores and measuring either the mass of the quantity of particle cores and/or the mass of the detached structures. This method is preferred because it may be applied to pillared particles of any material.

The SMF may be affected by, for example, the average dimensions of the structures, their porosity and the percentage coverage of the particle core by the structures (the structure density).

The SMF is preferably greater than or equal to 5%, more preferably at least 10%, most preferably at least 20%. The SMF is preferably no more than 95%, more preferably no more than 80%. Most preferably the SMF is 20-60%, especially 25-50%. A higher SMF value means that the high capacity active structures make a larger contribution to the active mass of a device of which they form a part, such as an electrode, and provide a higher overall capacity per unit mass can be obtained. However, if the SMF value is too high then the cost of manufacturing the structured particles may increase so that the cost to performance ratio of the electrode materials becomes uncompetitive, the structures may become too densely packed and/or the mechanical/electronic integrity of the pillar to core connection may be weakened.

If the material of the particle core has a density significantly different from the density of the material forming the structures, then the Structure Volume Fraction (SVF) may be measured instead of SMF, although it will be appreciated that SVF is applicable to the cases in which the core and structure densities are substantially the same (in which case the SVF value will be substantially the same as the SMF value) and the case in which the core and structure densities are significantly different. The SVF is given by the following equation:

$$SVF=[(\text{Total volume of structures extending from the particle core})/(\text{Total volume of structured particle})]\times 100\%$$

Similar methods to those used for measuring SMF may be used to measure SVF. Moreover, SVF may be derived from SMF measurements using a ratio of densities of the core material and the structure material. The volumes of the structures and the structured particles are the volumes which do not include volumes of open pores. Closed pores or voids that are completely enclosed within the bulk of a core or structure are included in the volumes. Accordingly, if the structures or cores are porous, the porosity may need to be measured. Example techniques that may be used to measure porosity include mercury porosimetry and Barret-Joyner-Halenda (BJH) analysis.

The degree of porosity is proportional to the amount of void space contained within the first particle component and is generally a reflection of the amount of void space present in the surface portion and is suitably at least 20% of the total volume of the surface portion, preferably less than 80%, for example 30 to 70 vol %. It will therefore be appreciated that the coating or filler will occupy some or all of the void space present in the surface portion of the first particle component upon the formation of a composite particle.

The volumes and dimensions of the structures and of the structured particles may be measured using a MasterSizer system or other similar laser diffractometry device, as described above. In an exemplary process, the volume of a structured particle is measured; structures are detached from the structured particles by a mechanical process such as ultrasonication; and the volume of the structures is measured. In the case of porous structures or cores, the porosity is determined and the measured volume is adjusted. For example, if porosity is 5% then measured volume is adjusted by 0.95 to give a solid volume. The volumes may also be measured using 2D digital imaging systems such as Morphologi, as described above, though they typically are unable to resolve particles with a dimension below 0.5 µm.

The SVF may be affected by, for example, the average dimension of the structures and the percentage coverage of the particle core by the structures (the structure density) and the density of the particle core and structure materials. The SVF is preferably greater than or equal to 5%, more preferably at least 10%, most preferably at least 20%. The SVF is preferably no more than 95%, more preferably no more than 80%. Most preferably the SVF is 20-60%, especially 25-50%. A higher SVF value means that the high capacity active structures make a larger contribution to the active mass of the electrode and a higher overall capacity per unit volume can be obtained. However, if the SVF value is too high then the cost of manufacturing the structured particles may increase so that the cost to performance ratio of the electrode materials becomes uncompetitive, the structures may become too densely packed and/or the mechanical/electronic integrity of the structure to core connection may be weakened.

The particles can also be characterised by their specific surface area, which may be measured by various techniques including BET (Brunauer, Emmett and Teller) and laser diffractometry.

The surface portion of the first particle component may comprise pores or voids with an opening to the surface with a principal dimension in the range 1 nm to 5 µm. The pores may be at least 2 nm, or at least 5 nm. The pores may have a size no more than 2 µm.

The specific surface area, area per unit mass, or BET value of a powder formed from a plurality of the first particle components is preferably reduced by the application of the removable filler, so that the first particle components can be more easily mixed into a composite material.

Preferably the BET of plurality of first particle components with the temporary filler is no more than 200 $m^2/g$, more preferably it is no more than 100 $m^2/g$, or no more than 80 $m^2/g$. Most preferably it is no more than 50 $m^2/g$ or less than 30 $m^2/g$. Preferably the percentage ratio of the BET value after application of the filler to the BET value without the filler is no more than 90%, preferably no more than 80%, more preferably no more than 60%. The active material of the first particle component suitably comprises an electroactive material. Preferably the first particle component comprises an electroactive material selected from the group comprising silicon, tin, germanium, gallium, lead, zinc and aluminium and electroactive alloys and compounds thereof. It is especially preferred that the first particle component comprises silicon, an electroactive alloy or compounds containing silicon and oxygen, compounds containing silicon and nitrogen, compounds containing silicon and fluorine, tin, tin alloys, compounds containing tin and oxygen, compounds containing tin and nitrogen, and compounds containing tin and fluorine. Examples of structured particles comprising the first particle component include but are not limited to pillared particles, porous particles, porous particle fragments and fibres as defined herein. It is especially preferred that the first particle component comprises structured particles selected from the group comprising silicon comprising pillared particles, porous particles, porous particle fragments and silicon comprising fibres or mixtures thereof. A first particle component comprising a silicon pillared particle is especially preferred.

It will be appreciated that the body portion of the first particle component may be devoid of structural features, comprise fewer structural features than the surface portion or have a different structure to that of the surface portion. The body portion suitably defines a core, which supports the structural features of the surface portion. The body portion suitably has principal dimension or diameter in the range 0.1 to 40 µm, preferably 1 to 35 µm, more preferably 5 to 30 µm and especially 5 to 20 µm. The size of the body portion may vary according to the application to which the composite particle is put. Where the composite particle is included in a composite electrode, the body portion suitably has principal dimension or diameter in the range 0.1 to 40 µm, preferably 1 to 35 µm, more preferably 5 to 30 µm and especially 5 to 20 µm.

Filler

The removable filler may completely or partially occupy the one or more voids in the surface portion. Complete occupation of a void should be understood to mean that voids including the filler are full or the meniscus of the filler bulges above the void opening. Partial occupation of a void should be understood to include situations in which the filler provides a thin coating on some of the void walls, situations where the filler merely provides a thin coating on the void walls, situations in which the filler occupies a significant volume within the void, but where the meniscus of the filler extends up the walls of the void and situations in which the filler has a substantially flat meniscus and occupies a significant volume within the void. Where the composite particle is used in battery applications, the removable filler suitably remains in place until it has either been used in the formation of a composite electrode or until formation of a battery cell is complete.

A removable filler may comprise a material that either sublimes or disintegrates at or above a temperature used to dry a composite material including the composite particle. Typically the removable filler sublimes or disintegrates at or above 50° C., preferably between 70 and 200° C., preferably 80 to 110° C., more preferably 90 to 100° C. Alternatively or in addition, the removable filler may be soluble in a liquid used to wash a composite material including the composite particle electrode or in a liquid, which supports a device including the composite material. Preferably the liquid in which the filler is soluble is selected from the group comprising an electrolyte, an electrolyte solvent or an ionic liquid. By the term "ionic liquid" it should be understood to mean a salt, which is liquid below 100° C. By the term "electrolyte" it should be understood to mean a solution of a salt in a polar solvent. By the term "electrolyte solvent" it should be understood to mean a polar solvent, which is capable of solubilising an organic or inorganic salt. Examples of electrolyte solvents include polar solvents such as water, an alcohol and an organic carbonate. Non-aqueous electrolyte solvents are preferred. Examples of non-aqueous electrolyte solvents that can be used include non-protic organic solvents such as N-methylpyrrolidone, propylene carbonate, ethylene carbonate, butylene carbonate, dimethyl carbonate, diethyl carbonate, gamma butyro lactone, 1,2-dimethoxy ethane, 2-methyl tetrahydrofuran, dimethylsulphoxide, 1,3-dioxolane, formamide, dimethylformamide, acetonitrile, nitromethane, methylformate, methyl acetate, phosphoric acid tri-ester, trimethoxy methane, sulpholane, methyl sulpholane and 1,3-dimethyl-2-imidazolidione.

Where the filler is soluble in an electrolyte is it suitably soluble in an electrolyte having a salt concentration of at least 0.7M, preferably a salt concentration in the range 0.7 to 2M. Examples of electrolyte salts include but are not limited to LiCl, LiBr, LiI, $LiClO_4$, $LiBF_4$, $LiB_{10}C_{20}$, $LiPF_6$, $LiCF_3SO_3$, $LiAsF_6$, $LiSbF_6$, $LiAlCl_4$, $CH_3SO_3Li$ and $CF_3SO_3Li$.

Examples of removable fillers, which remain in place until the final manufacturing stages of the composite electrode include organic or inorganic materials, which have a higher melting point than and a similar boiling or sublimation point to that of the slurry solvent and which are also insoluble therein. The removable filler suitably remains in place during the manufacture of a composite material including the composite particle. The filler may be subsequently removed together with the slurry solvent during a drying step. Alternatively, the removable filler may comprise an organic or inorganic material, which undergoes dissolution only when the composite particle is placed in a device of which it forms a part. Preferably the composite particle is used in the manufacture of battery cells and the filler dissolves in the electrolyte or electrolyte solvent on formation of the battery cell.

Examples of materials that can be used to fully or partially coat a first particle component and which can be removed once a composite electrode has been formed include o- and p-cresol, 3-nonanol, 1-methyl cyclohexanol, p-toluenenitrile, 2-methoxyphenol, 2-phenol-2-propanl, 2,3-dimethylanisole, phenol, 2,4-diemthylphenol, 3,4,4-trimethylpentanol, carboxyl acids such as oxalic acid and butanediol. These coating or filling materials suitably have a melting point of between 20 and 30° C. and a boiling point of 150 to 200° C. The coating material is suitably removed by sublimation, evaporation or degradation simultaneously with or subsequent to removal of the slurry solvent during the drying stage of electrode manufacture. The use of higher boiling point solids is preferred as this introduces additional porosity into the final electrode structure.

Examples of materials that can be used to fully or partially coat a first particle component and which can be removed by dissolution in a solvent (such as an electrolyte solvent) on inclusion in a device include waxes and surfactants. These coatings must be soluble in the solvent and must be stable under the operating conditions of the device. Where the composite particle is used in the manufacture of a lithium ion battery, the wax or surfactant must be stable under the voltage range at which the battery is cycled.

Examples of suitable waxes include natural wax such as 12-hydroxystearic acid, synthetic wax such as low molecular weight polyethylene, petroleum waxes such as paraffin wax, and microcrystalline waxes.

Examples of surfactants include carboxylic acid esters, carboxylic acid amides, sulfonic acid esters, sulfonic acid amides, particularly fatty acid esters and amides and alkyl sulfonic acid esters and amides. The surfactant may comprise a fluorinated compound. Preferably the surfactant comprises a perfluorinated compound.

It may be beneficial to combine a wax, a wax mixture or a surfactant as described above with other inorganic compounds, such as Li2CO3, LiF, Li.3PO4, SiO2, Li4SiO4, LiAlO2, Li2TiO3, LiNbO3 and the like, to improve both air stability and polar solvent stability. This means that the composite particle including the wax filler is easier to handle. Further the inclusion of an inorganic component provides the possibility of using commonly used polar solvents that dissolve commonly used polymer binders in the manufacture of a composite material. Waxes typically boil at temperatures in the range 120 to 200° C.

In a particularly preferred embodiment of the first aspect of the invention, the temporary coating is soluble in a solution of an organic carbonate or a mixture thereof but is insoluble or partially soluble in water and/or ethanol. Preferably the temporary filler or coating is soluble in a 0.5 to 2.5M solution of a salt in an organic carbonate; examples of suitable salt solutions in which the coating or filler is soluble include solutions of one or more salts selected from but not limited to the group comprising LiCl, LiBr, LiI, $LiClO_4$, $LiBF_4$, $LiB_{10}C_{20}$, $LiPF_6$, $LiCF_3SO_3$, $LiAsF_6$, $LiSbF_6$, $LiAlCl_4$, $CH_3SO_3Li$ and $CF_3SO_3Li$ or a mixture thereof in an organic carbonate.

The composite particles of the first aspect of the invention can be prepared using techniques that are well known to a person skilled in the art. Such techniques include micro-encapsulation techniques such as pan coating, centrifugal extrusion, spray drying, in-situ polymerisation and oligomerisation techniques, dip coating and sol-gel coating.

Preferably the first particle component is a pillared particle comprising a particle core with pillars extending there from. The body portion essentially comprises the particle core and the surface portion is defined by the volume through which the silicon comprising pillars and one or more voids extend. Preferably the pillars are integrally formed with the particle core. Suitably the removable filler fully or partially occupies the voids surrounding the pillars. Where the filler is removed on composite electrode formation, it has been found that evaporation of the filler has the effect of pulling the other components of the electrode material into or adjacent the voids of the first particle component thereby to enhance the internal connectivity of the electrode material. Where the filler is soluble only in the electrolyte solution of a battery, it has been found that dissolution of the filler results in superior wetting of the active material compared to materials that are not so coated, thereby enhancing the conductivity of a battery including a structured active particle. Further, the presence of a filler in the voids of the first particle component has been found to prevent detachment of the pillars from the core during the manufacture of both the composite electrode and a battery.

The diameter and length of the pillars comprised in the pillared particle will depend on the application to which the pillared particle is to be put. Where the pillared particle is to be included in a composite electrode for inclusion in a lithium ion secondary battery, for example, the pillars will typically have a diameter of greater than 10 nm, suitably a diameter in the range 30 to 500 nm, preferably 40 to 400 nm, more preferably 40 to 150 nm. The pillar length will suitably be in the range 0.5 to 10 μm, preferably 1 to 5 μm. Pillared particles having an overall diameter (core plus pillar length) in the range 0.5 to 40 μm, preferably 1 to 25 μm, more preferably 2 to 15 μm, especially 3 to 5 μm have been found to be suitable for secondary battery applications.

Where the first particle component is a porous particle comprising voids distributed over the surface and optionally into the volume of the particle, the surface portion essentially comprises the region (or volume) of the particle into which the coating or filler penetrates; where the particle is a sphere, this will typically be defined by the outer volume of the sphere. The body portion will consequently be defined by the volume (typically the inner or core volume) of the particle that has not been penetrated by the filler or coating. Where a filler or coating penetrates the entirety of the particle volume, it will be appreciated that the body portion will comprise a negligible volume compared to the volume occupied by the surface portion. It will, therefore, be understood that where the structured particle is a porous particle, the structural features comprise pores, voids or channels extending fully or partially into the volume of the particle and the coating or filler is distributed partially or completely within the voids.

As indicated above, a temporary filler promotes intimate connectivity between components such as a pillared particle or a porous particle and the other components of a material of which they form a part. The temporary filler also improves the homogeneity of the composite material by preventing aggregation.

The first particle component may (as described herein above) be in the form of an elongate element such as a fibre, wire, thread, tube, flake or ribbon as defined herein having structural features and voids distributed over the surface thereof. As stated herein above, elongate particles may be characterised by a smaller dimension, a larger dimension and an aspect ratio (the ratio of the larger dimension to the smaller dimension). Suitably the minor (smallest) dimension of the elongate element, given by its diameter or thickness, is at least 10 nm, preferably at least 30 nm. The aspect ratio of the elongate element is suitably at least 2:1, preferably at least 3:1, more preferably at least 5:1. Preferably the elongate element is provided in the form of a fibre, more preferably a porous fibre. Elongate elements according to the first aspect of the invention will typically comprise a body portion and a surface portion. Where the first particle component is a porous fibre, the body portion comprises that internal volume of the core, which is devoid of pores, voids or channels. The surface portion comprises the outer volume of the fibre, which is defined in part by the depth to which the pores or voids extend.

It will be appreciated that the average number and diameter of pores, voids or channels distributed over the surface of the first particle component will depend upon the application in which the composite particle is to be used. Where the composite particle is to be included in a composite material for use in the manufacture of a secondary battery, the pores, voids or channels provided distributed over the surface of the first particle component preferably have a diameter in the range 1 nm to 1500 nm, preferably 3.5 to 750 nm and especially 50 nm to 500 nm. The surface portion of the first particle component suitably has a porosity in the range 10 to 70%, preferably 20 to 50% and the number and diameter of the pores, voids and channels is sufficient to reflect this.

As indicated herein above, the material from which the body portion is formed may be the same or different to that of the surface portion. Where the composite particle or first particle component is to be used in battery applications, the surface portion of the first particle component suitably comprises an electroactive material. Preferably the surface portion is formed from an electroactive material selected from the group comprising silicon, gallium, germanium, aluminium, lead, tin, selenium, tellurium, boron and zinc or electroactive oxides, nitrides, hydrides, fluorides, alloys, compounds and mixtures thereof, especially silicon. The body portion may comprise an electroactive or a non-electroactive material. Where the body portion comprises an electroactive material, this may be the same or different to the electroactive material of the surface portion. The body and surface portions of the first particle component may be formed integrally, either by etching structural features into a surface portion of a starting particle or by growing structural features onto a body portion. In a first preferred embodiment of the first aspect of the invention, both the body portion and the surface portion comprise silicon or an electroactive alloy or compound of silicon. In a second preferred embodiment, the body portion comprises a first electroactive material and the surface portion comprises a second electroactive material having a composition different to that of the first electroactive material of the body portion.

The surface and/or body portion of the first particle component according to the first aspect of the invention may also or alternatively comprise, as indicated herein, compounds or mixtures of electroactive materials, which are themselves electroactive. Examples of suitable electroactive compounds or mixtures include but are not limited to BC, BSi, Si—C, SiGe, SiSn, GeSn, WC, $SiO_x$, $SnO_x$, lithium titanium oxides, $TiO_2$, binary metal oxides, BN, BAs, AlN, AlP, AlAs, AlSb, GaN, GaP, GaAs, GaSb, InN, InP, InAs, ZnO, ZnS, ZnSe, ZnTe, CdS, CdSe, CdTe, BeSe, BeTe, GeS, GeSe, GeTe, SnS, SnSe, SnTe, PbO, PbSe, PbTe, AgF, AgCl, AgBr, AgI, $BeSiN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$ or $Al_2CO$.

The first particle component may have an aspect ratio (ratio of the largest dimension to the smallest dimension) in the range 1:1 to 1:1000, preferably 1:1 to 1:100, more preferably 1:1 to 1:50. It will therefore be appreciated that the composite particle of the first aspect of the invention will also have a shape and aspect ratio that is the same as or is substantially similar to that of the first particle component from which it comprises.

The composite particle of the first aspect of the invention may optionally be combined with one or more additional components and formed into a composite electroactive material for inclusion as a composite layer in the formation of an electrode, preferably an anode. The first particle component will also typically have a principal diameter or thickness in the range 100 nm to 100 μm.

The composite particles according to the first aspect of the invention may be readily prepared and a second aspect of the invention provides a method of fabricating a composite particle according to the first aspect of the invention, the method comprising the steps of contacting a first particle component as defined above with a removable filler thereby to form a composite particle in which the filler completely or partially fills said voids. Suitable techniques for contacting the first particle component with the filler include micro-encapsulation techniques such as pan coating, air suspension coating, centrifugal extrusion, spray drying, in-situ polymerisation or oligomerisation techniques, dip-coating and sol-gel coating.

Where the removable filler is a liquid at room temperature, the liquid filler can be directly mixed with the first particle component. Alternatively, where the removable filler is a solid at room temperature, the filler may be provided in the form of a solution to infuse the voids of the first particle component. Preferably the filler or coating infuses into the pores, channels or voids of the first particle component. Where the coating or filler is a liquid at room temperature, the coated particle is dried and stored at a reduced temperature. Where the coating or filler material is a solid at room temperature and is insoluble in the solvent used to form a slurry, the composite particle can either be formed by warming the coating material to form a flow-able liquid or by dissolving the filler material in a suitable solvent, preferably an organic solvent before contacting the filler with the first particle component. The conditions used to ensure efficient infusion of the filler into and around the structural features will depend, in part, on the dimensions of the structural features of the first particle component and the viscosity of the filler solution and will be readily determined by a person skilled in the art. Where the pore dimensions or pillar separations are particularly small or where significant penetration of the filler is difficult due to the size of the particle, it may be appropriate to heat a solution of the filler to reduce its viscosity sufficiently to ensure that it infuses into the voids of the surface portion as completely as possible. In a preferred embodiment of the second aspect of the invention a pillared particle is mixed with a removable filler to form a composite particle.

Where the filler is removable on formation of a composite electrode, the filler will suitably be formed from a material that is insoluble in a solvent used to form the slurry at the temperature at which a composite electrode is formed; the filler suitably has a boiling point or sublimation point that is greater than the temperature at which the electrode is formed, preferably a temperature that is similar to or greater than that of the boiling point of the slurry solvent. An example of a material that can be removed on formation of the composite electrode is oxalic acid. The first particle component is mixed with a solution of oxalic acid, filtered and dried. Aqueous solutions of oxalic acid having a strength in the range 0.001 to 10 wt % may be used, preferably 0.05 to 5 wt %, more preferably 0.05 to 0.5 wt %.

An example of a filler that can be removed on formation of a device includes a surfactant such as a perfluoro-alkyl carboxylic acid or sulfonic acid ester such as a perfluoro-octane sulfonic acid ester. The first particle component is mixed with an aqueous solution of the surfactant as described above and formed into a composite electrode. Aqueous solutions of surfactant having a strength in the range 0.001 to 10 wt % may be used, preferably 0.05 to 5 wt %, more preferably 0.05 to 0.5 wt %.

It will be appreciated that the methods employed to contact the filler with the first particle component will depend, in part, upon the nature of the filler materials.

Where the filler is removable either on drying the composite electrode or through dissolution in the electrolyte solvent of a battery of which the first particle component forms a part, the filler is suitably contacted with the first particle component by forming a slurry of the first particle component in a solution of the filler and gently agitating the slurry to form a slurry including the composite particle. Solutions of the filler material can be readily prepared for filler materials having a melting point of not less than 15° C. above room temperature, preferably not less than 10° C. above room temperature by gently heating a filler/solvent mixture prior to contacting the solution with the first particle component. Preferably the first particle component is mixed with a filler or a solution of the filler at a similar temperature to that of the filler in order to promote efficient infusion of the filler into the voids of the surface portion of the first particle component. The temperature can be increased on mixing if necessary. The resulting liquid slurry including a composite particle is suitably dried to remove or substantially remove the slurry solvent to give composite particles in the form of individual particles, an aggregate or a dispersion. The concentration of the filler in the solvent may depend, in part, on the size of the filler molecules; a large molecular weight filler is suitably provided in a lower concentration solution compared to coating materials comprising lower molecular weight components as this improves the extent to which the molecule infuses into the first particle component.

As mentioned herein above, due to their resilient nature, the composite particles referred to herein can be used in the manufacture of devices such as electrochemical cells, metal ion batteries such as lithium-ion batteries, lithium air batteries, flow cell batteries, other energy storage devices such as fuel cells, thermal batteries, photovoltaic devices such as solar cells, filters, sensors, electrical and thermal capacitors, microfluidic devices, gas/vapour sensors, thermal or dielectric insulating devices, devices for controlling or modifying the transmission, absorption or reflectance of light or other forms of electromagnetic radiation, chromatography or wound dressings and a third aspect of the invention provides the use of a composite particle according to the first aspect of the invention in the manufacture of any one of these devices.

As mentioned herein above, the composite particles referred to herein can be used in the manufacture of a composite material and a fourth aspect of the invention provides a method of fabricating a composite material, the method comprising the steps of forming a composite mix comprising a composite particle according to the first aspect of the invention and applying the composite mix to a substrate. Preferably the composite material is an electrode material. Preferably the composite mix is an electrode mix. Preferably the substrate is a current collector. The coated current collector is suitably dried. The drying step may effect removal of the temporary filler. A fifth aspect of the invention provides a composite electrode comprising a current collector having a layer of an electrode material applied thereon, wherein the electrode material comprises a composite particle according to the first aspect of the invention.

The composite particles of the first aspect of the invention can be used in the manufacture of battery cells, preferably in the manufacture of secondary battery cells and a sixth aspect of the invention provides a battery comprising an anode, a cathode, a separator and an electrolyte, wherein the anode comprises a current collector having an electrode material provided thereon, the electrode material comprising a composite particle according to the first aspect of the invention.

The batteries of the sixth aspect of the invention are readily manufactured and a seventh aspect of the invention provides a method of fabricating a battery cell, the method comprising providing a cell housing, an anode comprising an electrode material comprising a composite particle according to the first aspect of the invention, a cathode, a separator and an electrolyte, disposing the separator between the anode and the cathode, placing the anode, cathode and separator in the cell housing and filling the cell housing with electrolyte.

The invention also provides an electrode material comprising a composite particle according to the first aspect of the invention and, optionally, one or more components. Suitable components for inclusion into an electrode material include but are not limited to a binder and a conductive component. Preferably the binder is selected from but not limited to the group comprising polyvinylidene fluoride (PVDF), sodium carboxymethyl cellulose (NaCMC), polyacrylic acid (PAA), sodium polyacrylate (NaPAA), styrene butadiene rubber (SBR), lithium polyacrylate (LiPAA) and polyimide. In a further embodiment, the invention also provides a method of fabricating an electrode material, the method comprising the steps of providing a composite particle according to the first aspect of the invention and combining the composite particle with one or more selected components selected from but not limited to a binder and a conductive carbon.

The invention provides in a further eighth aspect of the invention a composition comprising a stable suspension of composite particles according to the first aspect of the invention or a composite material according to the fourth aspect of the invention in a carrier liquid in which the filler does not degrade or dissolve. The compositions according to the eighth aspect of the invention can be used to store or transport composite particles, particularly structured particles as defined in the first aspect of the invention. Where the composition according to the eighth aspect of the invention is used to store or transport composite particles or structured particles as defined in the first aspect of the invention, the filler suitably includes a surfactant, which helps to maintain the composite particles in suspension for prolonged periods of time. The solvent used to support the suspension may be a polar or a non-polar solvent. Further the solvent may suitably comprise a gel-able component, which facilitates the formation of a gel suspension, thereby increasing the stability of a composition according to the eighth aspect of the invention still further.

The invention will now be described with reference to the accompanying drawings and examples in which:

FIG. 1 is a composite particle comprising as a first particle component, a pillared particle (1), having a particle core (2) and a plurality of pillars (3) extending there from. A filler (4) occupies the void space (5) between adjacent pillars. Although not illustrated, partial filling of voids may involve the formation of a thin coat of filler on the void walls.

FIG. 2 is a composite particle comprising as a first particle component a porous particle (6) or a porous particle fragment (6a) having a plurality of voids or pores (7, 7a). A filler (8, 8a) occupies some or all of the void spaces within the particle (6) or particle fragment (6a). The depth (from the surface of the particle) to which the filler penetrates is defined as the surface region.

EXAMPLES

Figure 1:
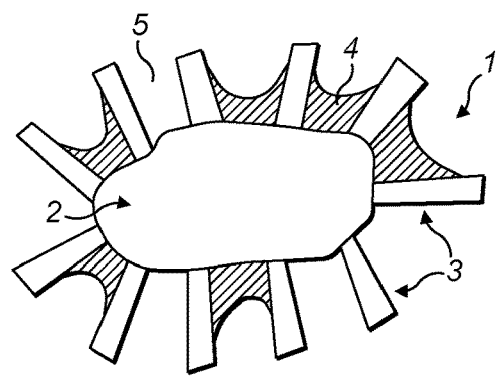
Figure 2:
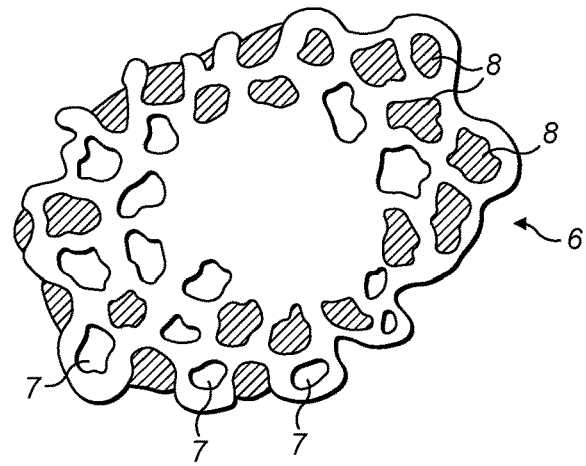
Figure 3:
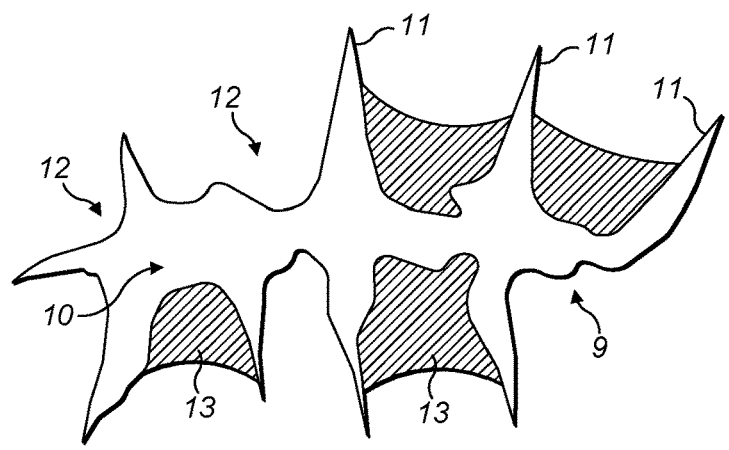
FIG. 3 is a composite particle comprising as a first particle component a fractal (9), being a porous particle fragment, the fractal comprising a body portion (10) and a plurality of spikes (11) extending there from. Void spaces (12) separate the spikes (11) and are fully or partially occupied by filler (13).
Figure 4:
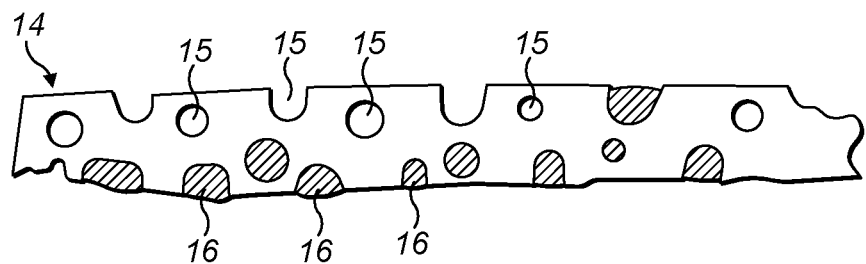
FIG. 4 is a composite particle comprising as a first particle component a fibre core (14) having pores (15) formed on the surface thereof, each pore defining a void in the surface structure. The voids are either fully or partially occupied by a filler (16).
Figure 5:
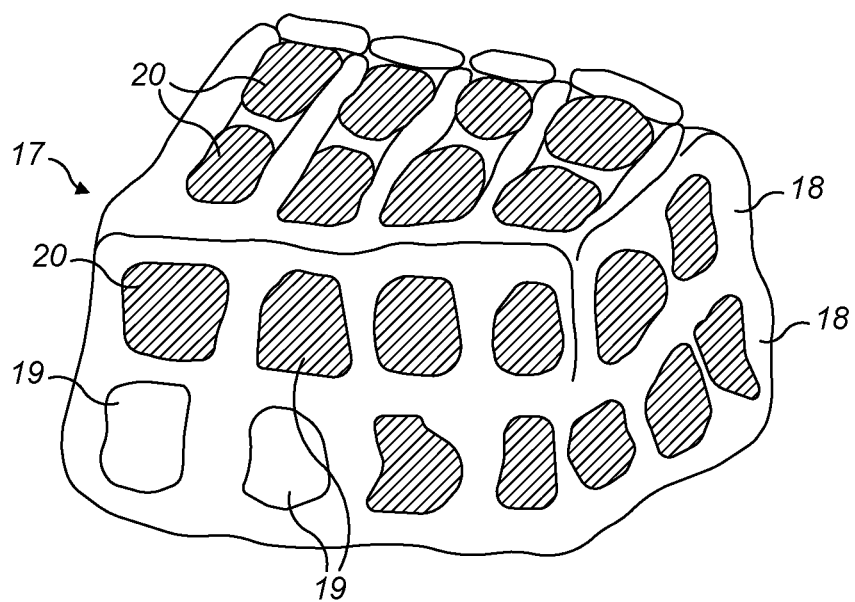
FIG. 5 is a composite particle comprising as a first particle component a scaffold structure (17) including a plurality of elongate structures (18) bounding void spaces (19). The void spaces (19) are occupied by a filler (20).

Example 1—Formation of a Polyacrylic Acid Polyethylene Glycol Ester

Example 1a

An ester of polyacrylic acid and polyethylene glycol (MW=4000) was dissolved in deionised water. The final solution contained 0.05 wt % polyacrylic acid/polyethylene glycol ester.

Example 2—Formation of a Perfluoro-Octane Sulfonic Acid Ester Solution

Perfluoro-octane sulfonic acid ester was dissolved in an aqueous solution to give a final solution containing 0.05 wt % of perfluoro-octane sulfonic acid ester.

Suitable surfactants are sold by 3M as FC4330, which contains fluoroaliphatic polymeric esters.

Example 3a—Formation of Coated Particles

Silicon pillared particles having an average D50 value in the range 3 to 10 µm were added to a solution as described in Examples 1 or 2 and stirred for between 2 and 3 hours. The wet particles were separated from the bulk mixture by filtration. The coated particles were then dried in an airstream until dry. The resulting particles were characterised by the presence of either an oxalic acid or a perfluoro-octane sulfonic acid ester.

Example 3b—Electrode Mix

A slurry was formed by shear mixing 85 parts by weight of spherical synthetic graphite (d50=27 µm), 3 parts by weight of VGCF, 9.2 parts by weight of a composite silicon particle (9 parts silicon particle as specified in Example 1 and 0.005 parts oxalic acid), and 2.8 parts by weight of a PVdF(9200) binder in NMP as the carrier liquid using a T25 IKA High Shear Mixer® 15. The final solids content of the slurry is in the range 30 to 50%. The viscosity of the slurry is in the range 1000 to 4500 mPa·s. The resulting slurry was cast onto a copper foil to a thickness of 60 g/cm2.

Example 3c

The procedure was repeated using a perfluoro-octane sulfonic acid ester to give a composite having perfluoro-octane sulphonic acid coated silicon particles.

Example 4—Preparation of Cells

Electrode and Cell Fabrication
Anode Preparation

The desired amount of composite particle was added to a carbon mixture that had been bead milled in deionised water as specified above. The resulting mixture was then processed using a T25 IKA High Shear® overhead mixer at 1200 rpm for around 3 hours. To this mixture, the desired amount of binder in solvent or water was added. The overall mix was finally processed using a Thinky™ mixer for around 15 minutes to give the composite materials described in Examples 3a and 3b above.

The anode mixture (either 3a or 3b) was applied to a 10 µm thick copper foil (current collector) using a doctor-blade technique to give a 20-35 µm thick coating layer. The resulting electrodes were then allowed to dry. Composite materials comprising oxalic acid released $CO_2$ gas during the drying process.
Cathode Preparation The cathode material used in the test cells was a commercially available lithium MMO electrode material (e.g. Li1+xNi0.8Co0.15Al0.05O2) on a stainless steel current collector.
Electrolyte The electrolyte used in all cells was a 1.2M solution of lithium hexafluorophosphate dissolved in solvent comprising a mixture of ethylene carbonate and ethyl methyl carbonate (in the ratio 3:7 by volume) (82%), FEC (15 wt %) and VC (3 wt %). The electrolyte was also saturated with dissolved CO2 gas before being placed in the cell.
Cell Construction
"Swagelok" test cells were made as follows:
Anode and cathode discs of 12 mm diameter were prepared and dried over night under vacuum.
The anode disc was placed in a 2-electrode cell fabricated from Swagelok® fittings.
Two pieces of Tonen separator of diameter 12.8 mm and 16 um thick were placed over the anode disc.
40 µl of electrolyte was added to the cell.
The cathode disc was placed over the wetted separator to complete the cell.
A plunger of 12 mm diameter containing a spring was then placed over the cathode and finally the cell was hermetically sealed. The spring pressure maintained an intimate interface between the electrodes and the electrolyte.
The electrolyte was allowed to soak into the electrodes for 30 minutes.
Structured silicon particles including a coating of pefluorobenzene sulphonic acid ester were observed to have lost their coating material on formation of a cell.

The invention claimed is:

1. A composite particle comprising a first particle component and a second particle component in which:
    (a) the first particle component comprises a body portion and a surface portion, the surface portion comprising one or more structural features and one or more voids, wherein the one or more structural features and the one or more voids extend between the body portion and a particle boundary of the composite particle, whereby the surface portion and body portion define together a structured porous or pillared particle; and
    (b) the second particle component consists of a removable filler that is removable from the composite particle during processing;
    characterised in that (i) the one or more structural features of the surface portion comprise an electroactive material comprising a member selected from the group consisting of silicon, tin, germanium, gallium, lead, zinc and aluminium; (ii) the filler is contained around the one or more structural features and within the one or more voids comprised within the surface portion of the first particle component; and (iii) the filler has a sublimation or disintegration temperature of at least 50° C. and/or is soluble in an ionic liquid or an electrolyte solution.

2. The composite particle according to claim 1, wherein the filler is soluble in an electrolyte solution having a salt concentration of at least 0.7 M.

3. The composite particle according to claim 1, wherein the filler is soluble in a solution comprising a member selected from the group consisting of N-methylpyrrolidone, propylene carbonate, ethylene carbonate, butylene carbonate, dimethyl carbonate, diethyl carbonate, gamma butyro lactone, 1,2-dimethoxy ethane, 2-methyl tetrahydrofuran, dimethyl sulphoxide, 1,3-dioxolane, formamide, dimethylformamide, acetonitrile, nitromethane, methylformate, methyl acetate, phosphoric acid trimester, trimethoxy methane, sulpholane, methyl sulpholane and 1,3-dimethyl-2-imidazolidione.

4. The composite particle according to claim 1, wherein the filler sublimes or degrades at a temperature in the range 70 to 200° C.

5. The composite particle according to claim 1, wherein the removable filler comprises a member selected from the group consisting of o- and p-cresol, 3-nonanol, 1-methyl cyclohexanol, p-toluenenitrile, 2-methoxyphenol, 2-phenol-2-propanol, 2,3-dimethylanisole, phenol, 2,4-diemthylphenol, 3,4,4-trimethylpentanol, butanediol, oxalic acid, a surfactant and a natural wax or a synthetic wax selected from the group comprising 12-hydroxystearic acid, low molecular weight polyethylene, petroleum waxes such as paraffin wax, and microcrystalline waxes.

6. The composite particle according to claim 1, wherein the first particle component is selected from a pillared particle, a porous particle having voids distributed there through, a porous particle fragment or a fractal, or a scaffold structure.

7. The composite particle according to claim 6, wherein the first particle component is the pillared particle and wherein the surface portion comprises one or more pillars distributed over a body portion.

8. The composite particle according to claim 6, wherein the first particle component is the pillared particle and wherein the voids of the surface portion comprise channels extending from the body portion to the particle boundary.

9. The composite particle according to claim 6, wherein the first particle component is the porous particle having voids distributed there through and wherein the porous particle is a fibre, wire, thread, tube, flake, or ribbon with a minor dimension of at least 10 nm.

10. The composite particle according to claim 6, wherein the first particle component is the porous particle having voids distributed there through and further comprising voids distributed at the surface of the particle.

11. The composite particle according to claim 1, wherein the particle has a principal diameter in the range 0.5 to 10 µm.

12. The composite particle according to claim 1, wherein the body portion and the surface portion are formed integrally and the active material comprising the body portion is the same as or is similar to the active material of the surface portion.

13. The composite particle according to claim 1, wherein the active material of the body portion is different to the active material of the surface portion.

14. The composite particle according to claim 1, wherein the active material is an electroactive material.

15. The composite particle according to claim 1, wherein the electroactive material is silicon, a silicon alloy or an electroactive silicon compound.

16. A method of forming a composite particle according to claim 1, the method comprising steps of mixing the first particle component with the filler in liquid form.

17. The method according to claim 16, wherein the filler is provided in a solution comprising a solvent and wherein the solvent is removed by evaporation.

18. A composite material comprising:
a composite particle, the composite particle comprising a first particle component and a second particle component in which:
(a) the first particle component comprises a body portion and a surface portion, the surface portion comprising one or more structural features and one or more voids, wherein the one or more structural features and the one or more voids extend between the body portion and a particle boundary of the composite particle, whereby the surface portion and body portion define together a structured particle; and
(b) the second particle component comprises a removable filler;
characterised in that (i) the one or more structural features of the surface portion comprise an electroactive material comprising a member selected from the group consisting of silicon, tin, germanium, gallium, lead, zinc and aluminium; (ii) the filler is contained around the one or more structural features within one or more voids comprised within the surface portion of the first particle component; and (iii) the filler has a sublimation or disintegration temperature of at least 50° C. and/or is soluble in an ionic liquid or an electrolyte solution; and a binder; and optionally further comprising one or more components selected from an electroactive carbon, a conductive carbon and an electroactive component.

19. A composition comprising:
a stable suspension of a composite particle, the composite particle comprising a first particle component and a second particle component in which:
(a) the first particle component comprises a body portion and a surface portion, the surface portion comprising one or more structural features and one or more voids, wherein the one or more structural features and the one or more voids extend between the body portion and a particle boundary of the composite particle, whereby the surface portion and body portion define together a structured particle; and
(b) the second particle component comprises a removable filler;
characterised in that (i) the one or more structural features of the surface portion comprise an electroactive material comprising a member selected from the group consisting of silicon, tin, germanium, gallium, lead, zinc, and aluminium; (ii) the filler is contained around the one or more structural features within one or more voids comprised within the surface portion of the first particle component; and (iii) the filler has a sublimation or disintegration temperature of at least 50° C. and/or is soluble in an ionic liquid or an electrolyte solution; and
wherein the stable suspension is in a liquid carrier; and optionally wherein the removable filler includes a surfactant to maintain the composite particles in a stable suspension.

20. The composite particle according to claim 1, wherein the filler is soluble in an electrolyte solution having a salt concentration of between about 0.7 and about 2 M.

21. The composite particle according to claim 1, wherein the filler sublimes or degrades at a temperature in a range between about 70 and about 110° C.

22. The composite particle according to claim 1, wherein the body portion comprises an electroactive material.

23. The composite particle according to claim 1, wherein the electroactive material comprises an electroactive alloy of a member selected from the group consisting of silicon, tin, germanium, gallium, lead, zinc, and aluminium.

24. The composite particle according to claim 1, wherein the electroactive material comprises a compound comprising a member selected from the group consisting of silicon, tin, germanium, gallium, lead, zinc, and aluminium.

* * * * *